United States Patent
Barber et al.

(10) Patent No.: US 9,821,127 B2
(45) Date of Patent: Nov. 21, 2017

(54) CHILD-RESISTANT CLOSURE SYSTEMS FOR CONTAINERS

(71) Applicant: TAPTANGO, LLC, Gainesville, VA (US)

(72) Inventors: Launce R. Barber, Richmond, VA (US); Thomas J. A. Zuber, Fort Lee, NJ (US); Corey R. Vaughan, Seattle, WA (US)

(73) Assignee: TAPTANGO, LLC, Richmond, VA (US)

( * ) Notice: Subject to any disclaimer, the term of this patent is extended or adjusted under 35 U.S.C. 154(b) by 31 days.

(21) Appl. No.: 14/846,914

(22) Filed: Sep. 7, 2015

(65) Prior Publication Data
US 2015/0374934 A1    Dec. 31, 2015

Related U.S. Application Data

(63) Continuation of application No. 14/216,639, filed on Mar. 17, 2014, now abandoned.
(Continued)

(51) Int. Cl.
*B67B 1/00* (2006.01)
*A61M 11/00* (2006.01)
(Continued)

(52) U.S. Cl.
CPC ...... *A61M 11/006* (2014.02); *A61M 15/0025* (2014.02); *A61M 15/08* (2013.01);
(Continued)

(58) Field of Classification Search
CPC .. A61M 15/00; A61M 15/0025; A61M 15/08; A61M 15/009; A61M 2205/27;
(Continued)

(56) References Cited

U.S. PATENT DOCUMENTS

| 3,435,975 A | 4/1969 | Weigand |
| 3,514,003 A | 5/1970 | Fitzgerald |

(Continued)

OTHER PUBLICATIONS

U.S. Office Action for U.S. Appl. No. 14/216,639, dated Mar. 10, 2015, 9 pages.
(Continued)

*Primary Examiner* — Patrick M Buechner
(74) *Attorney, Agent, or Firm* — Patent Law of Virginia, PLLC; Brian J. Teague

(57) ABSTRACT

A child-resistant closure system for a container comprises a protective cap, a dispensing tip, and a cylindrical base. The dispensing tip includes a pair of buttons adapted to control whether the dispensing tip is in a locked condition so as to prevent actuation or an unlocked condition so as to permit actuation, via the shoulders, of a sprayer pump unit that is partially contained within the dispensing tip. The cylindrical base has a pair of spaced apart upwardly extending legs. In an locked condition of the dispensing tip, the upwardly extending legs are not aligned with slots defined in a horizontal circumferential portion of the dispensing tip such that downward movement of the dispensing tip in relation to the base is blocked by the upwardly extending legs to prohibit actuation of the sprayer pump unit and to lock the dispensing tip.

6 Claims, 14 Drawing Sheets

Related U.S. Application Data

(60) Provisional application No. 61/801,831, filed on Mar. 15, 2013.

(51) Int. Cl.
*A61M 15/08* (2006.01)
*B05B 11/00* (2006.01)
*A61M 15/00* (2006.01)

(52) U.S. Cl.
CPC ...... *B05B 11/3049* (2013.01); *B05B 11/3059* (2013.01); *A61M 15/009* (2013.01); *A61M 2205/276* (2013.01)

(58) Field of Classification Search
CPC ......... A61M 2205/276; B05B 11/3049; B05B 11/3059; B05B 11/306
USPC .................................................. 222/153.13
See application file for complete search history.

(56) References Cited

U.S. PATENT DOCUMENTS

| | | | |
|---|---|---|---|
| 3,690,519 A | | 9/1972 | Wassilieff |
| 3,797,705 A | * | 3/1974 | Cooprider ........... B05B 11/3059 222/153.13 |
| 3,827,606 A | * | 8/1974 | Knickerbocker ... B05B 11/3059 222/153.13 |
| 4,065,036 A | * | 12/1977 | Kirk, Jr. .............. B05B 11/3059 222/153.13 |
| 4,162,746 A | * | 7/1979 | Anderson ........... B05B 11/3059 166/270.1 |
| 4,244,495 A | | 1/1981 | Lorscheid et al. |
| 4,368,830 A | * | 1/1983 | Soughers ............. B05B 11/306 222/153.13 |
| 4,480,762 A | | 11/1984 | Thomas |
| 4,801,093 A | | 1/1989 | Brunet et al. |
| 4,830,224 A | * | 5/1989 | Brison ................ B05B 11/3059 222/153.06 |
| 4,944,429 A | | 7/1990 | Bishop et al. |
| 5,492,251 A | | 2/1996 | Albini et al. |
| 5,725,128 A | * | 3/1998 | Foster ................ B05B 11/3001 222/153.13 |
| 5,826,756 A | * | 10/1998 | Foster ................ B05B 11/3001 222/321.3 |
| 5,908,125 A | | 6/1999 | Opresco |
| 6,164,498 A | | 12/2000 | Faughey et al. |
| 6,612,450 B1 | | 9/2003 | Buono |
| 6,926,174 B1 | | 8/2005 | Heldt |
| 7,168,594 B2 | | 1/2007 | Law et al. |
| 8,104,643 B2 | | 1/2012 | Pruvot |
| 9,352,348 B2 | | 5/2016 | Greiner-Perth |
| 2005/0098172 A1 | | 5/2005 | Anderson |
| 2007/0080174 A1 | * | 4/2007 | Coe .................... B05B 11/3059 222/153.13 |
| 2007/0137649 A1 | * | 6/2007 | Matsumoto ........... B65D 83/54 128/205.23 |
| 2008/0142468 A1 | | 6/2008 | Delagrange |
| 2008/0210229 A1 | | 9/2008 | Corbacho |
| 2008/0245896 A1 | | 10/2008 | Welp |
| 2011/0240679 A1 | * | 10/2011 | Langlos .............. B05B 11/3049 222/321.7 |
| 2013/0175303 A1 | | 7/2013 | Donnette et al. |
| 2013/0270298 A1 | | 10/2013 | Dejonge |
| 2014/0263455 A1 | | 9/2014 | Keenan |
| 2015/0088069 A1 | * | 3/2015 | Kim .................... A61M 15/08 604/149 |
| 2015/0284177 A1 | | 10/2015 | Patil et al. |
| 2016/0243319 A1 | * | 8/2016 | Szymiczek ......... B05B 11/0032 |

OTHER PUBLICATIONS

USPTO Office Action in U.S. Appl. No. 14/216,668, dated Aug. 15, 2017, 22 pages.

\* cited by examiner

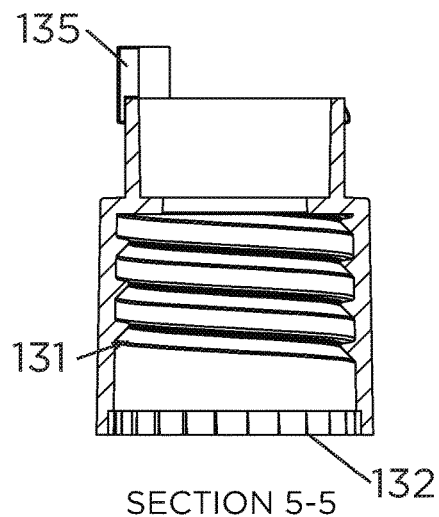
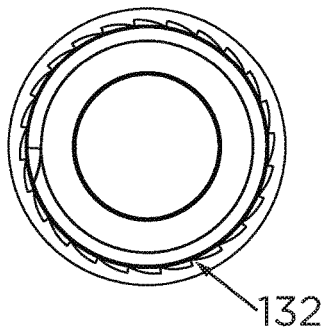
FIG. 5       FIG. 6
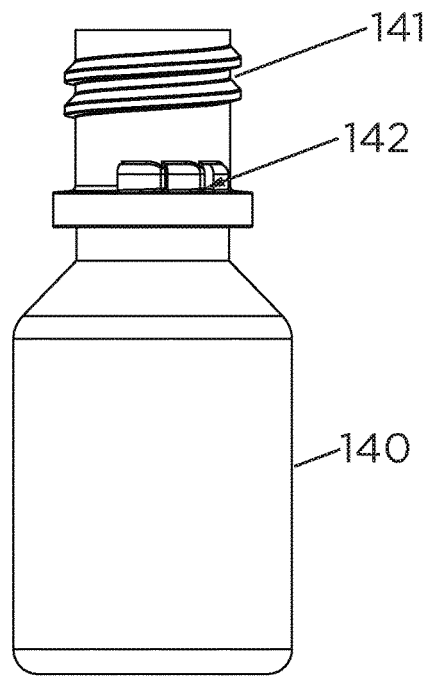
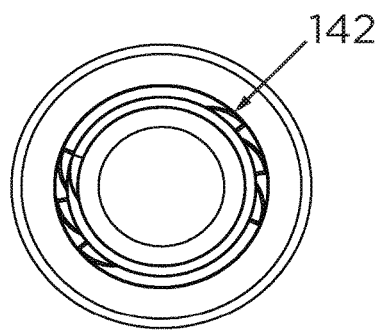
FIG. 7       FIG. 8

SECTION 18-18

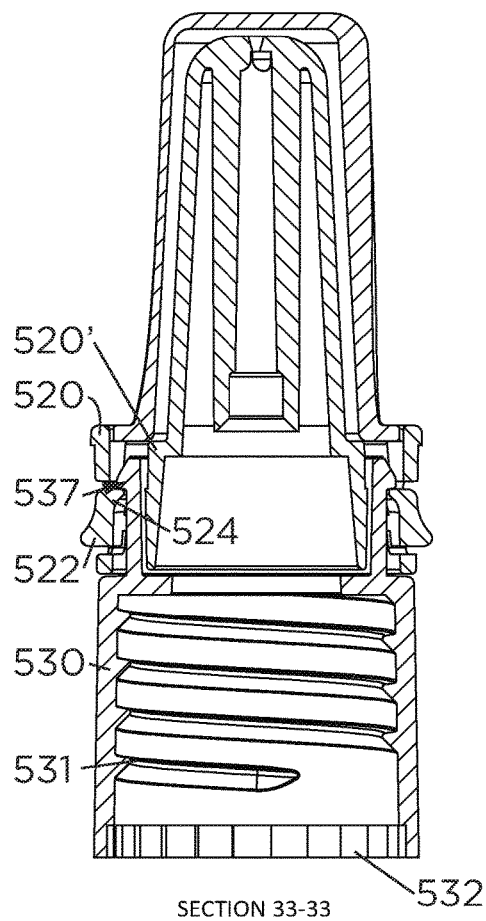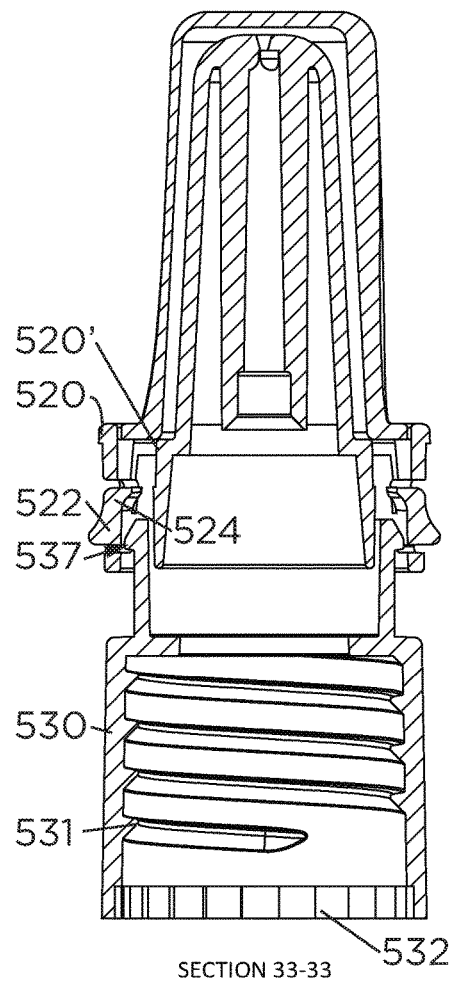
FIG. 33
FIG. 34

CHILD-RESISTANT CLOSURE SYSTEMS FOR CONTAINERS

CROSS-REFERENCE TO RELATED APPLICATION

The present application is a continuation of and claims priority to U.S. patent application Ser. No. 14/216,639, filed Mar. 17, 2014, which in turn claims the benefit under 35 U.S.C. §119(e) of U.S. Provisional Patent Application No. 61/801,831 to the inventors, filed Mar. 15, 2013, the entire contents of which are hereby incorporated by reference herein.

BACKGROUND

1. Field

Example embodiments in general relate to child-resistant closure systems for containers.

2. Related Art

The Consumer Product Safety Commission ("CPSC") proposed a rule in early 2012 to require child-resistant ("CR") packaging for any over-the-counter or prescription product containing the equivalent of 0.08 milligrams or more of an imidazoline, a class of drugs that includes tetrahydrozoline, naphazoline, oxymetazoline, and xylometazoline, in a single package. Imidazolines are a family of drugs that are vasoconstrictors indicated for nasal congestion and/or ophthalmic irritation. Products containing imidazolines can cause serious adverse reactions, such as central nervous system ("CNS") depression, decreased heart rate, and depressed ventilation in children treated with these drugs or who accidentally ingest them. Based on the scientific data, the CPSC has preliminarily found that availability of 0.08 milligrams or more of an imidazoline in a single package, by reason of its packaging, is such that special packaging is required to protect children under 5 years old from serious personal injury or illness due to handling, using, or ingesting such a substance. The CPSC has taken this action under the Poison Prevention Packaging Act of 1970.

Accordingly, as it is expected that this rule will become law, manufacturers will be required to develop child-resistant closure (CRC) systems for their nasal pump sprayers and eye-dropper dispenser products (such as Visine®), as each of these products contain the equivalent of 0.08 milligrams or more of an imidazoline. In doing so, one goal is to ensure that the newly developed dispensers are robust enough to prevent children five years old and under from being able to inadvertently open the bottle to use or ingest the contents, while still being "senior friendly" to mature adults.

Moreover, the same child-resistant principals as to be applied to nasal sprayers and eye-dropper (squeeze) bottles so as to comply with impending CR packaging regulations, could also be made applicable to other fields of fluid dispenser/packaging. For example, little or no thought has be given to developing CRC systems for consumer fluid pump dispensers having a viscosity generally higher than that of water or water-based medicinal fluids, such as those dispensers holding lotions, shampoos, baby oils, and paints.

SUMMARY

An example embodiment is directed to a child-resistant closure system for a pump sprayer. The system includes a protective cap, a dispensing tip configured to receive the cap thereon, a lower end of the dispensing tip including a pair of finger-depressing shoulders in opposite relation to one another, each shoulder extending horizontally outward from the dispensing tip, with a cylindrical portion provided beneath the shoulders to serve as a bottom end of the dispensing tip, the cylindrical portion including a pair of buttons spaced 180° apart on a vertical facing of the cylindrical portion, the buttons adapted to control whether the dispensing tip is in a locked or unlocked condition so as to permit actuation, via the shoulders, of a sprayer pump unit that is partially contained within the dispensing tip, each button including an undercut formed on a back face thereof within the interior of the dispensing tip, and a cylindrical base having its upper end secured to the dispensing tip and its lower end configured to be secured to a dispenser bottle which contains fluid, the dispensing tip and base housing the sprayer pump unit therein which is actuated by depressing the shoulders on the dispensing tip once the dispensing tip is in an unlocked condition, the base top end including a circular thread formed around its circumference on an external surface thereof. In a locked condition of the dispensing tip, the undercuts on the back faces of the buttons engage an underside of the circular thread on the base to prohibit actuation of the sprayer pump unit and to lock the dispensing tip. To achieve an unlocked condition of the dispensing tip to permit actuation of the sprayer pump unit via depressing the shoulders, the buttons are pressed simultaneously to deflect the undercuts outward and away from the circular thread on the base, permitting the dispensing tip to move upward to a home dispensing position under a force applied to the dispensing tip from a spring in the sprayer pump unit.

BRIEF DESCRIPTION OF THE DRAWINGS

Example embodiments will become more fully understood from the detailed description given herein below and the accompanying drawing, wherein like elements are represented by like reference numerals, which are given by way of illustration only and thus are not limitative of the example embodiments herein.

FIG. 2 is a front view of a dispensing tip according to the system of FIG. 1.

FIG. 5 is a sectional view 5-5 taken from FIG. 4

FIG. 6 is a bottom perspective view of the base shown in FIG. 4.

FIG. 7 is a dispensing bottle usable with the system of FIG. 1.

FIG. 8 is a top view of the bottle shown in FIG. 7.

FIG. 33 is a sectional view 33-33 taken from FIG. 31 to show a locked position.

FIG. 34 is a sectional view 33-33 taken from FIG. 31 to show an unlocked position.

DETAILED DESCRIPTION

Figure 1:
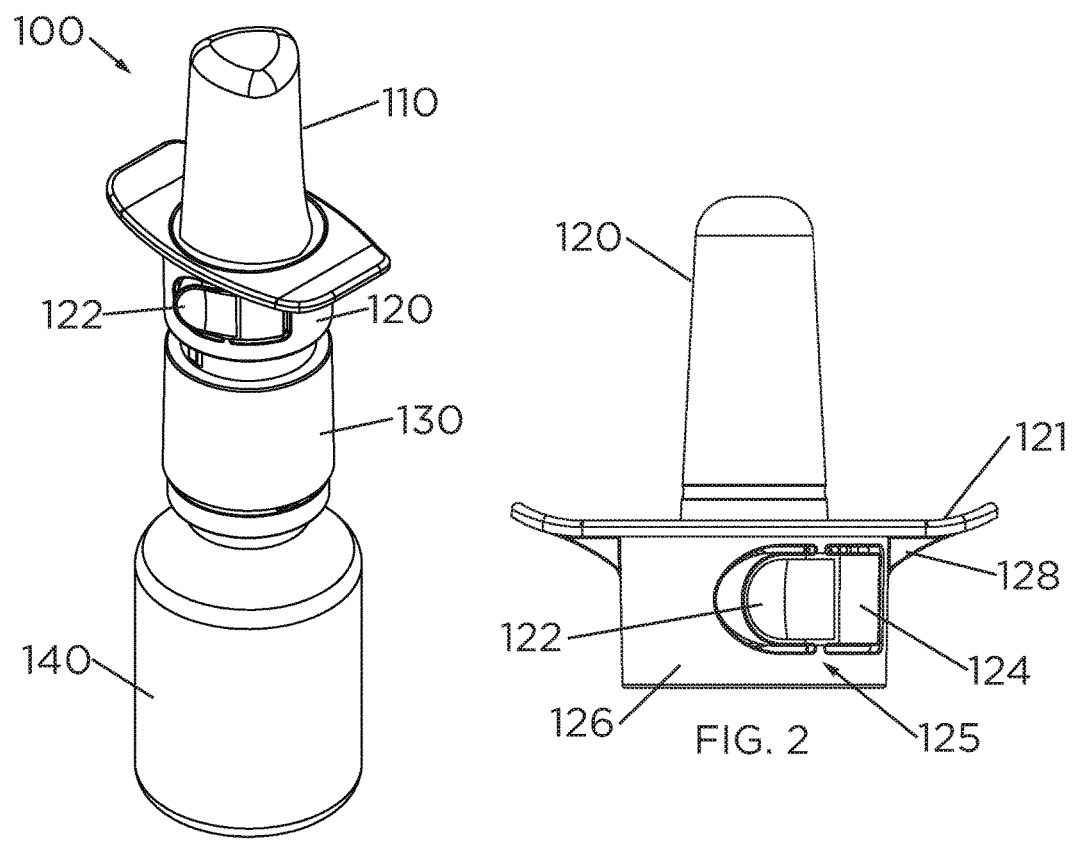
FIG. 1 is a front view of a child-resistant closure system for a pump sprayer according to an example embodiment.

FIG. 1 is a front view of a child-resistant closure system for a pump sprayer according to an example embodiment. The child-resistant closure (CRC) system 100 includes a cap 110, a dispensing tip 120 and a base 130. Each of the cap 110, dispensing tip 120 and base 130 may be injection molded or extruded or otherwise formed of a suitable plastic material, as is known. The cap 110 is 3-sided to minimize rolling and avoid losing the cap 110. The base 130 has interior grooves or threads for coupling it to a threaded member on dispenser bottle 140 which holds the medicinal fluid therein. The base 130 and dispensing tip 120 also partially enclose a sprayer pump unit 150 (not shown) which partly extends into the dispenser bottle 140 interior.

In an example, the CRC system 100 described here and child-resistant based embodiments to be described hereafter may be applicable, but not limited to: single or multi-dose dispensers such as nasal sprayers, ocular sprayers, dermal sprayers, misters, aerators, airless dispensers, air-use dispensers, spouted and non-spouted pump assemblies, and the like. The containers or dispensers foreseeable have applications in the healthcare, home and garden, beauty and food and beverage industries, thus the embodiments described herein are applicable to dispensers or containers configured for, but not limited to dispensing nasal medicine, sunscreens, food products, paints and protectants, deodorants, insect repellants, sealed breath fresheners, ear medicine, dermal medicine, lotions, fragrances, air fresheners, spray starches, oxygen, insecticides, fungicides, herbicides, rodenticides, spray oils, talcs, and spray food stuffs. Further, the CRC systems can be varied in size and applied as a platform to handle any desired viscosity of fluid.

Figure 3:
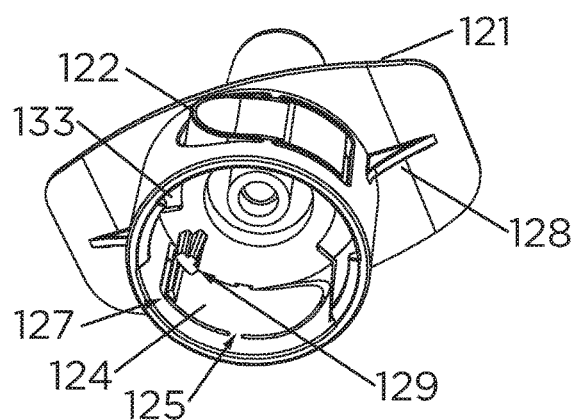
FIG. 3 is a bottom perspective view of the dispensing tip according to the system of FIG. 1.

FIG. 2 is a front view of a dispensing tip according to the system of FIG. 1, and FIG. 3 is a bottom perspective view of the dispensing tip according to the system of FIG. 1. Dispensing tip 120 includes a pair of spaced, dished buttons 122 on a collar 126 that permit locking and unlocking of the dispensing tip 120 for rotation thereof to allow dispensing via a pair of shoulders 121, which are used to depress the sprayer pump unit 150 within (not shown) under finger pressure, as is known. A button 122 is provided on either side of collar 126 and includes a relief 124 separated by a hinge 125 that acts as a cam when the button 122 is actuated by the user. A ramp 127 is positioned on the back side of each relief 124; this interfaces with an upstanding leg 135 that is formed on either side atop of base 130, as to be shown hereafter. A pair of internal catches 129 within dispensing tip 120 also come into contact with the legs 135 of the base 130 in a locked condition, locking out the dispensing tip 120. A pair of spaced apart slots 133 are defined in the dispensing tip 120.

Figure 4:
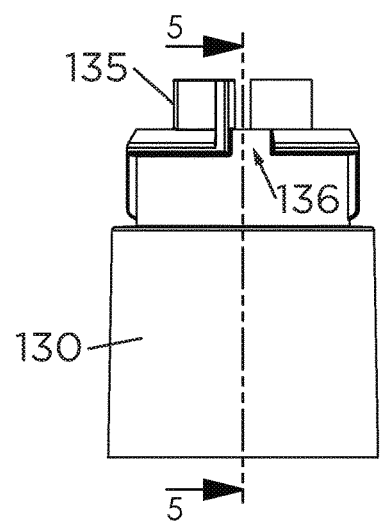
FIG. 4 is a side view of a base according to the system of FIG. 1.
Figure 12:
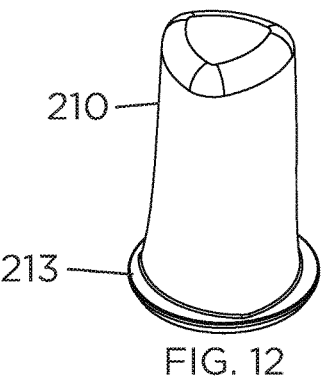
FIG. 12 is a perspective view of a cap according to the system of FIG. 11.

FIG. 4 is a side view of the base, FIG. 5 a sectional 5-5 taken from FIG. 4 of the base, FIG. 6 is a bottom perspective view of the base, FIG. 7 is a dispenser bottle usable with the system of FIG. 1, and FIG. 8 is a top view of the bottle shown in FIG. 12. Referring to FIGS. 4-8, the base 130 includes a pair of upstanding legs 135 in spaced relation on a top surface thereof, and includes a series of grooved internal threads 131 for coupling with a dispenser bottle 140. There is also a vertical clearing 136 adjacent each leg that is formed into base 130 that permits product dispensing. Additionally, an anti-back off feature has been added to both the dispenser bottle 140 and base 130. The base 130 is formed with internal threads 131, and serrated teeth 132 at its bottom skirt. Upon full seating of the base 130 to the bottle 140, the downward force of application will push the bottom skirt of the base 130 over formed teeth 142 in the bottle 140, providing a secure method of application where tampering to remove the base 130 would be evident and would eliminate accidental removal.

Figure 9:
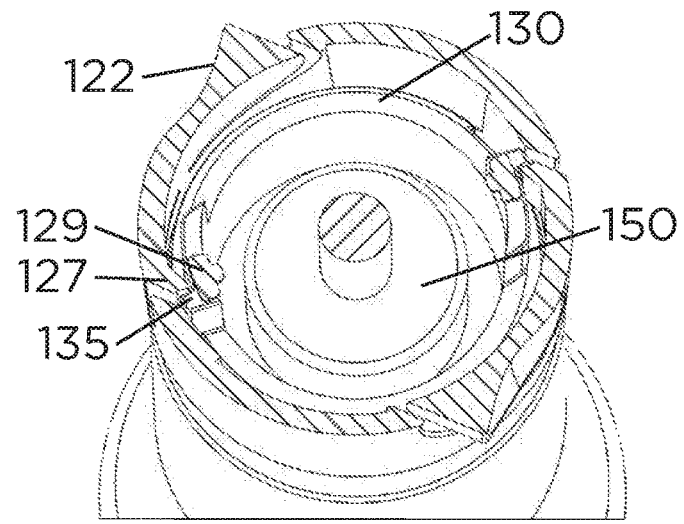
FIG. 9 is a portion of a cross-cut of the dispensing tip in the xz-plane to show positions of the base legs and buttons in a locked position.
Figure 10:
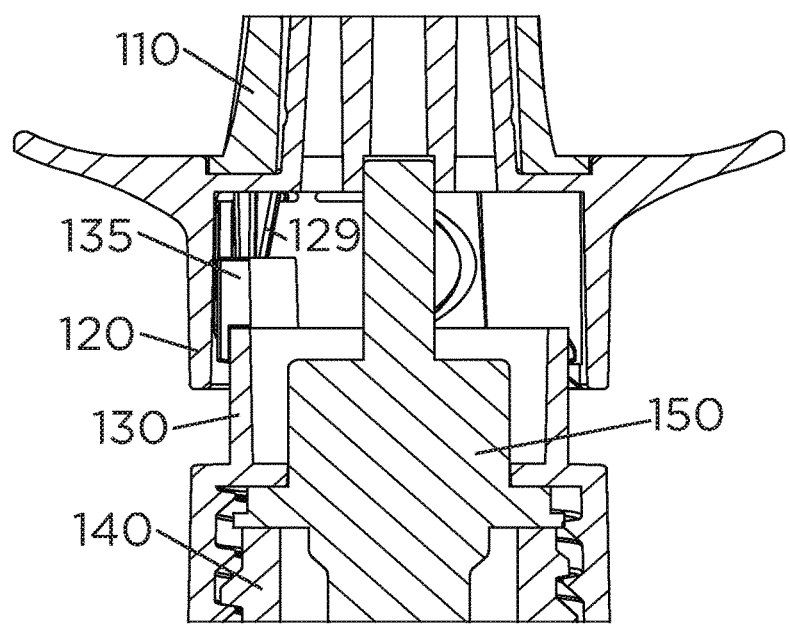
FIG. 10 is a portion of a sectional view of the system taken in the xy-plane to show a locked position.
Figure 9A:
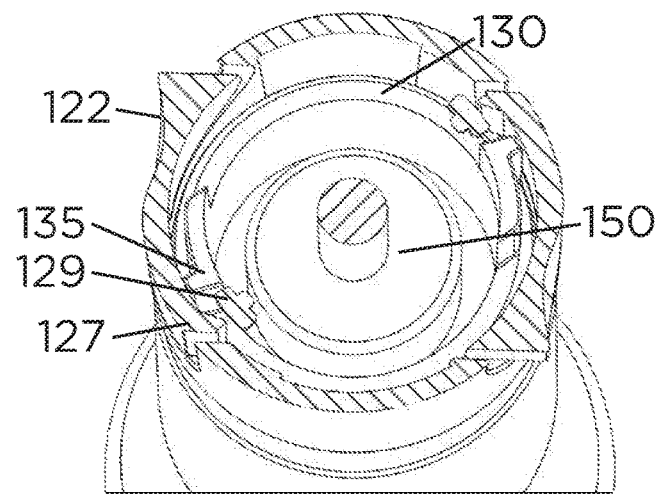
FIG. 9A is a portion of a cross-cut of the dispensing tip in the xz-plane to show positions of the base legs and buttons in an unlocked position.
Figure 10A:
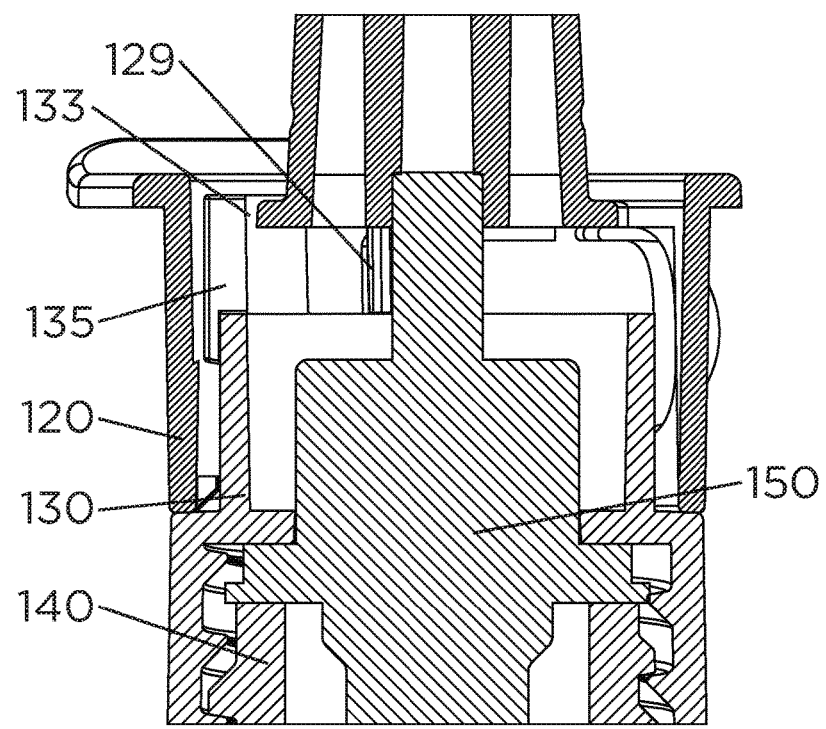
FIG. 10A is a portion of a sectional view of the system taken in the xy-plane to show an unlocked position.

FIG. 9 is a portion of a cross-cut of the dispensing tip in the xz-plane to show positions of the base legs and buttons in a locked position, FIG. 9A shows the portion of FIG. 9 in an unlocked position, FIG. 10 is a portion of a sectional view of the system taken in the xy-plane to show a locked position, and FIG. 10A shows the portion of FIG. 10 in an unlocked position. Referring to FIGS. 9, 9A, 10 and 10A, basic operations are described. The cap 110 is retained simply by an undercut on the dispensing tip 120. All that is required to remove cap 110 is a vertical pull.

FIG. 10 shows a locked condition with the leg 135 of the base 130 held by catch 129; FIG. 9 shows this in another orientation and additionally shows the tab 127 on the dispenser tip engaged with leg 135. Both horizontal dished buttons 122 on dispensing tip 120 are to be simultaneously depressed in order to release the dispensing mechanism. Depressing the buttons cants the ramps 127 outward via hinges 125, which releases the upstanding legs 135 on the base 130, allowing each leg 135 to turn and release from its corresponding catch 129. The dispensing tip 120 pivots 30° on center axis and aligns with the vertical clearing 136 on the base 130, which allows for product dispensing.

Although the embodiment shown in FIGS. 1-10 describes a base 130 having two legs that is twist to unlock, in which the dispenser tip 120 locks out actuation of a sprayer pump unit, the exact same embodiment can be accomplished with a dispenser 120 having two buttons, but actuating a single leg 135. The functions of locking and unlocking described above with a single leg having the same construction as leg 135 would accomplish the same goal of locking out dispensing, as the leg 135 would extend all the way to catch 129. The other side would by legless, but the interlock would still require simultaneous two-button interaction for child-resistant purposes.

Figure 11:
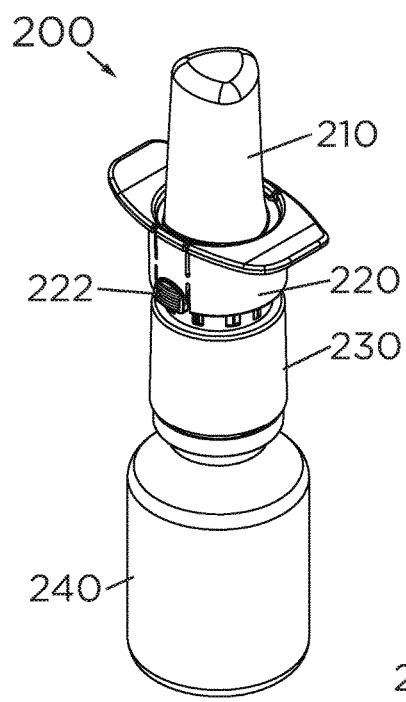
FIG. 11 is a perspective view of a child-resistant closure system for a pump sprayer according to another example embodiment.

FIG. 11 is a perspective view of a child-resistant closure system for a pump sprayer according to another example embodiment, and FIG. 12 is a perspective view of a cap according to the system of FIG. 11. Referring to FIGS. 11 and 12, the child-resistant closure (CRC) system 200 includes a cap 210, a dispensing tip 220 and a base 230. Each of the cap 210, dispensing tip 220 and base 230 may be injection molded or extruded or otherwise formed of a suitable plastic material, as is known. The cap 210 is 3-sided to minimize rolling and avoid losing the cap 210 and includes a lower rim 223.

The dispensing tip 220 includes two raised ribbed buttons 222 on opposite sides thereof that control whether the dispensing tip 220 is in a locked or unlocked condition so as to permit actuation of the sprayer pump unit 250 (not shown). The base 230 has interior grooves or threads for coupling it to a threaded member on dispenser bottle 240 which holds the medicinal fluid therein. The base 230 and dispensing tip 220 also partially enclose a sprayer pump unit 250 (not shown) which partly extends into the dispenser bottle 240 interior.

Figure 13:
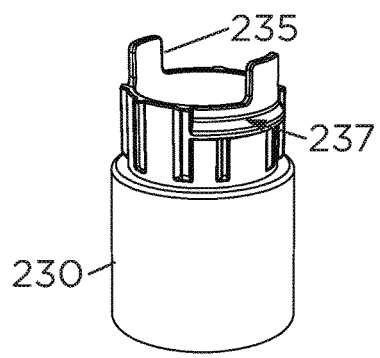
FIG. 13 is a perspective view of a base according to the system of FIG. 11.

FIG. 13 is a perspective view of a base according to the system of FIG. 11. The base 230 includes a pair of upstanding legs 235 in spaced relation on a top surface thereof, and includes a series of grooved internal threads (not shown) for coupling with a dispenser bottle 240. There is also a horizontal groove 237 outside each leg 235 to facilitate dispenser tip 220 rotation around the base 230 when rotating to an unlocked state to permit dispensing. The base 230 and dispenser bottle 240 have serrations similar to that shown in FIGS. 5-8; in other words, an anti-back off feature is included. The base 230 is formed with internal threads and serrated teeth at its bottom skirt. Upon full seating of the base 230 to the bottle 240, the downward force of application pushes the bottom skirt of the base 230 over formed teeth in the bottle 240, providing a secure method of application where tampering to remove the base 230 would be evident and would eliminate accidental removal.

Figure 14:
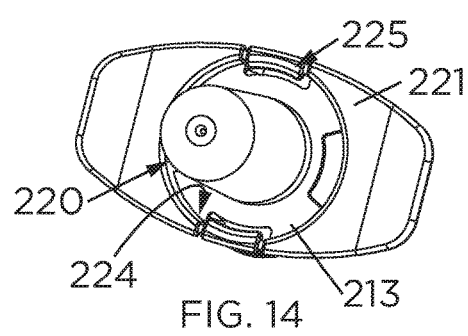
FIG. 14 is a perspective view of a dispensing tip according to the system of FIG. 11.

FIG. 14 is a perspective view of a dispensing tip according to the system of FIG. 11. The dispenser tip 220 includes shoulders 221 that is the finger-depressing surface for actuating the internal sprayer pump unit 250. The center between the shoulders 221 has a circular downward cutout 224 in which the rim 213 of the cap 210 can seat in. The upper ends of the buttons 222 includes catches 225 that clamp onto the rim 213 of the cap 210 seated in the circular cutout 224 to fixedly retain the cap 210.

Figure 15:
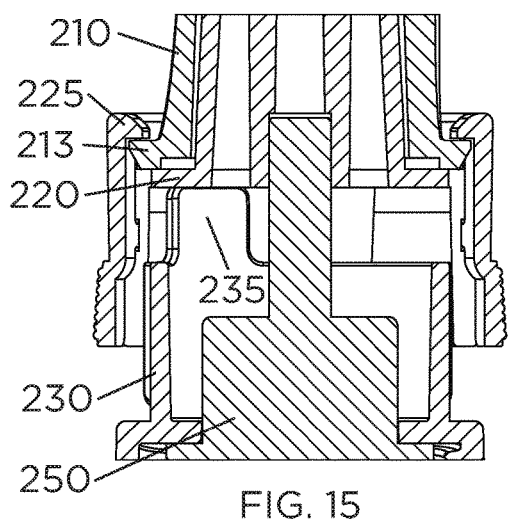
FIG. 15 is a portion of a sectional view of the system taken in the yz-plane to show a locked position.

FIG. 15 is a portion of a sectional view of the system taken in the yz-plane to show a locked position. In operation, both raised ribbed buttons 222 on dispensing tip to be depressed in order to release the top cap 210. Actuation is achieved through depression of the buttons 220 that twist the arms at the midpoint releasing the catches 225 that are slightly elevated from the cap deck of the dispensing tip 220. The cap 210 can then be removed.

However, the system 200 is still locked (as shown in FIG. 15) and will not dispense. To operate, the dispensing tip 200 needs to be rotated 30° to release the sprayer pump unit 250. The dispensing tip 220 is locked by the two vertical legs 235 that protrude from top surface of the base 230. When the dispensing tip 220 is rotated, reliefs (not shown in FIG. 15) cut though the dispensing tip 220 to allow the legs 235 to pass through on the dispensing stroke.

Figure 16:
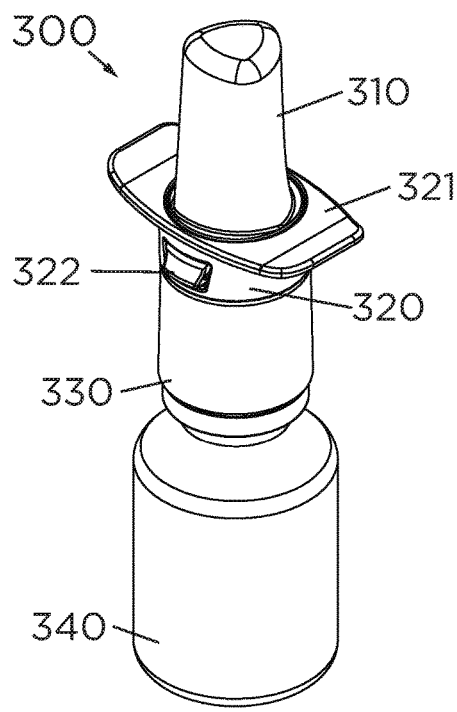
FIG. 16 is a perspective view of a child-resistant closure system for a pump sprayer according to another example embodiment.
Figure 17:
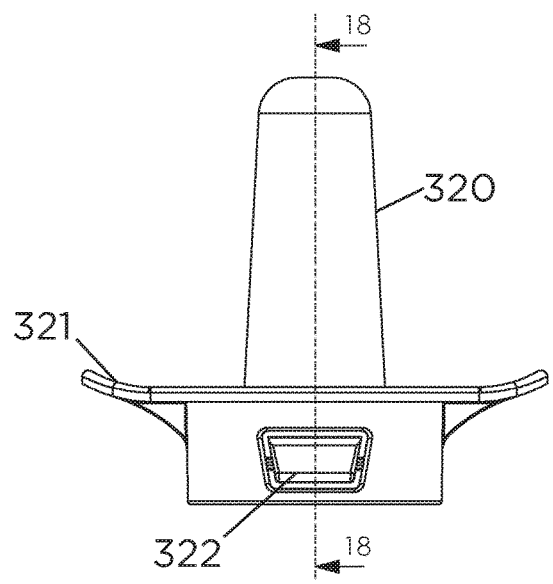
FIG. 17 is a front view of a dispensing tip according to the system of FIG. 16.
Figure 19:
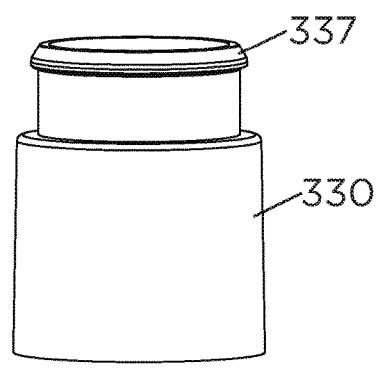
FIG. 19 is a front view of a base according to the system of FIG. 16.
Figure 18:
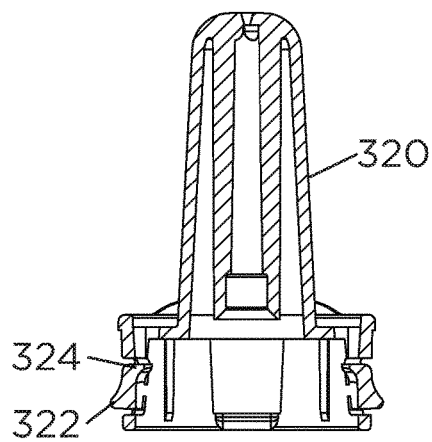
FIG. 18 is a sectional view 18-18 taken from FIG. 17.

FIG. 16 is a perspective view of a child-resistant closure system for a pump sprayer according to another example embodiment, FIG. 17 is a front view of a dispensing tip according to the system of FIG. 16, FIG. 18 is a sectional view 18-18 taken from FIG. 17, and FIG. 19 is a front view of a base according to the system of FIG. 16. Referring to FIGS. 16-19, the child-resistant closure (CRC) system 300 includes a cap 310, a dispensing tip 320 and a base 330. Each of the cap 310, dispensing tip 320 and base 330 may be injection molded or extruded or otherwise formed of a suitable plastic material, as is known. The cap 310 is 3-sided to minimize rolling and avoid losing the cap 310.

The dispensing tip 320 includes a pair of finger-depressing shoulders 321 in opposite relation thereto (180 degrees apart), as well as two buttons 322 on opposite sides of a cylindrical portion of the dispenser tip 320 below the shoulders 321 that control whether the dispensing tip 320 is in a locked or unlocked condition so as to permit actuation of the sprayer pump unit 350 (not shown) via the shoulders 321. An undercut 324 is formed on the back side of each button 322, the undercuts 324 are configured to interface and engage a single circular thread 337 at the top of a base 330. The base 330 has interior grooves or threads for coupling it to a threaded member on dispenser bottle 340 which holds the medicinal fluid therein. The base 330 and dispensing tip 320 also partially enclose a sprayer pump unit 350 (not shown) which partly extends into the dispenser bottle 340 interior.

Figure 20:
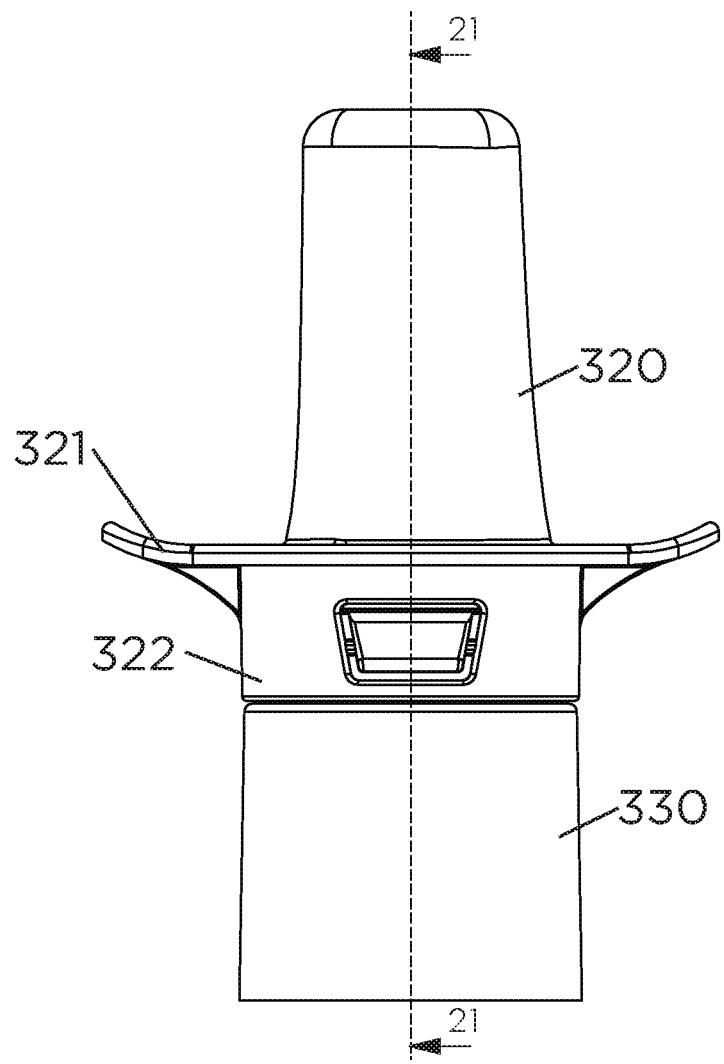
FIG. 20 is a front view of the dispensing cap and base of the system in FIG. 16.
Figure 21:
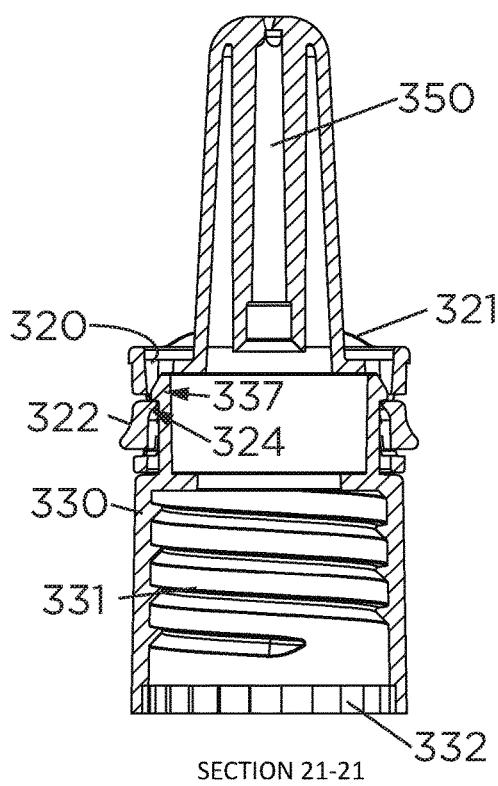
FIG. 21 is a sectional view 21-21 taken from FIG. 20 to show a locked position.
Figure 22:
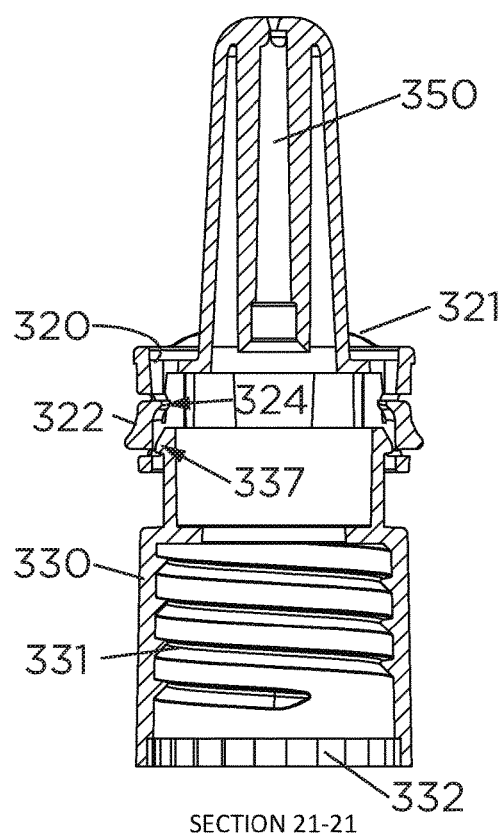
FIG. 22 is a sectional view 21-21 taken from FIG. 20 to show an unlocked position.

FIG. 20 is a front view of the dispensing tip and base of the system in FIG. 16, FIG. 21 is a sectional view 21-21 taken from FIG. 20 to show a locked position, and FIG. 22 is a sectional view 21-21 taken from FIG. 20 to show an unlocked position. Referring to FIGS. 20-22, in the 21-21 views the cap 310 is shown removed. This is because in this embodiment the cap 310 is not locked; it can be removed from the dispensing tip 320 by simply pulling upward. With the dispensing tip 320 in place, dispensing actuation is locked out. Specifically, the dispensing tip 320 is retained by the two undercuts 324, each undercut 324 located on the back face of two buttons 322 180° apart on the dispensing tip 320. The undercuts 324 engage with the underside of continuous, circular thread 337 at the top of the base 330, as shown in the locked configuration of FIG. 21. When engaging, the undercuts 324 will initially deflect outwards until they pass the thread 337, where after they will snap back to vertical and engage the underside of thread 337 of base 330, as shown.

To release the dispensing tip 320, the buttons 332 on the dispensing tip 320 must be pressed simultaneously, causing the undercuts 324 to once again deflect outwards. The dispensing tip 320 will move vertically (by force of the spring in the sprayer pump unit 350, shown obscured by the dispensing tip 320) to the home dispensing position. This is shown in FIG. 22. With the dispensing tip 320 now released, the sprayer pump unit 350 is now free to dispense a single dose via pressing down using one's fingers on the shoulders 321, as is known. For each dose, the dispensing tip 320 must be released.

Figure 23:
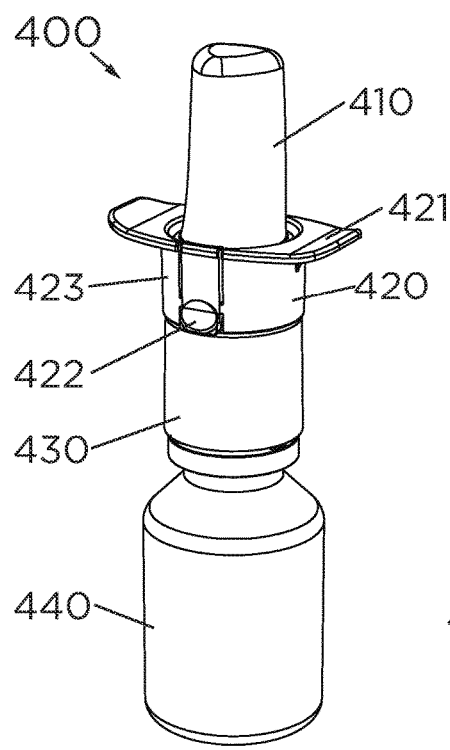
FIG. 23 is a perspective view of a child-resistant closure system for a pump sprayer according to another example embodiment.
Figure 24:
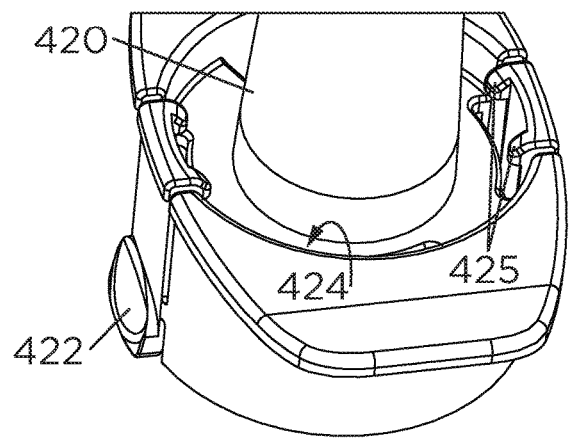
FIG. 24 is a partial side perspective view of a dispensing tip according to the system of FIG. 23.
Figure 25:
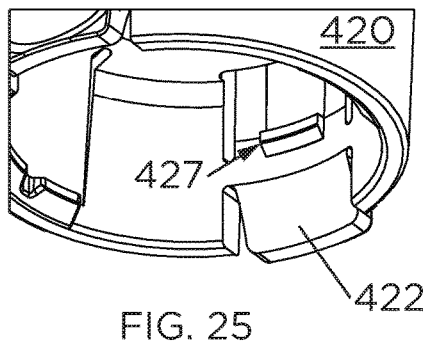
FIG. 25 is a partial bottom perspective view of the dispenser tip of FIG. 24.
Figure 26:
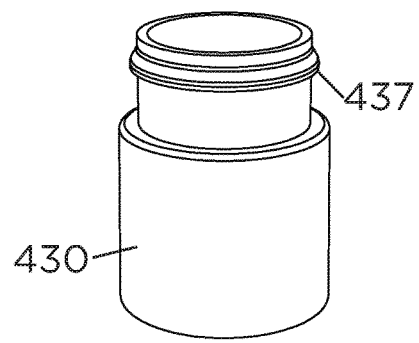
FIG. 26 is a front view of a base according to the system of FIG. 23.

FIGS. 21 and 22 also show the internal threads 331 and serrations 332 on the inside of the base 330. As previously shown in FIGS. 5-8, an anti-back off feature is added to both the bottle 340 and base 330. Upon full seating of the base 330 to the bottle 340, the downward force of application will push the bottom skirt of the bottle (containing serrations 332) over the formed teeth in the bottle 340, providing a secure method of application where tampering to remove the base 330 would be evident and would eliminate accidental removal thereof FIG. 23 is a perspective view of a child-resistant closure system for a pump sprayer according to another example embodiment, FIG. 24 is a partial side perspective view of a dispensing tip according to the system of FIG. 23, FIG. 25 is a partial bottom perspective view of the dispenser tip of FIG. 24, and FIG. 26 is a front view of a base according to the system of FIG. 23. Referring to FIGS. 23-26, the child-resistant closure (CRC) system 400 includes a cap 410, a dispensing tip 420 and a base 430. Each of the cap 410, dispensing tip 420 and base 430 may be injection molded or extruded or otherwise formed of a suitable plastic material, as is known. The cap 410 is 3-sided to minimize rolling and avoid losing the cap 410.

The dispensing tip 420 includes two levers 422 on opposite sides thereof that control whether the dispensing tip 420 is in a locked or unlocked condition so as to permit actuation of the sprayer pump unit 450 (not shown). A pair of slits or reliefs 424 are formed on either side of each lever 422 to provide flexibility. The dispensing tip 420 includes finger-depressing shoulders 421 which serve to engage the internal pump sprayer unit (not shown). Centrally located between the shoulders 421 is a circular recessed cutout 424 for receiving the rim of the cap 410 so that the cap 410 may be seated therein. As shown in FIGS. 24 and 25, each lever 422 includes two undercuts, on set on the top end of the lever 422, another undercut on a back side thereof. There is a top set of undercuts 425 that is designed to engage the rim of the cap 410 to secure the cap 410 into the recessed cutout 424 to lock out operation of the dispenser tip 420. There is a lower undercut 427 that engages a horizontal single thread rim 437 on the upper end of base 430 which also locks out actuator operation. Accordingly, user action on the levers 422 control the action of the undercuts 425, 427.

The base 430 has interior grooves or threads for coupling it to a threaded member on dispenser bottle 440 which holds the medicinal fluid therein. The base 430 and dispensing tip 420 also partially enclose a sprayer pump unit 450 (not shown) which partly extends into the dispenser bottle 440 interior.

Figure 27:
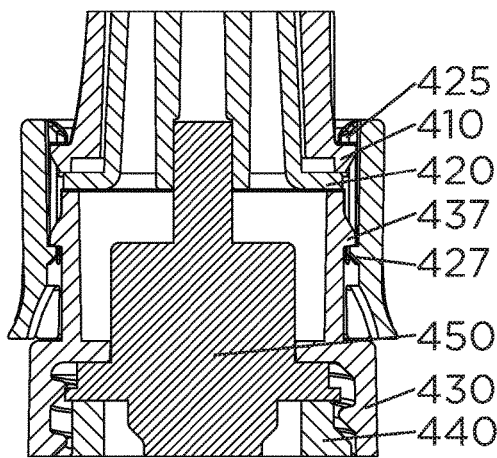
FIG. 27 is a portion of a sectional view of the system taken in the xz-plane to show a locked position.
Figure 28:
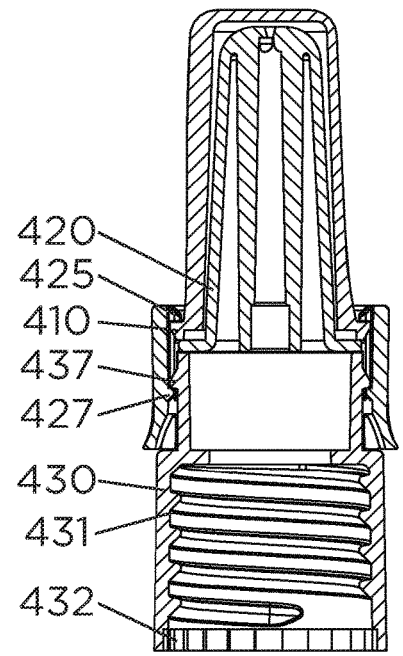
FIG. 28 is sectional view of the cap, dispenser tip and base taken in the xz-plane to show a locked position.
Figure 29:
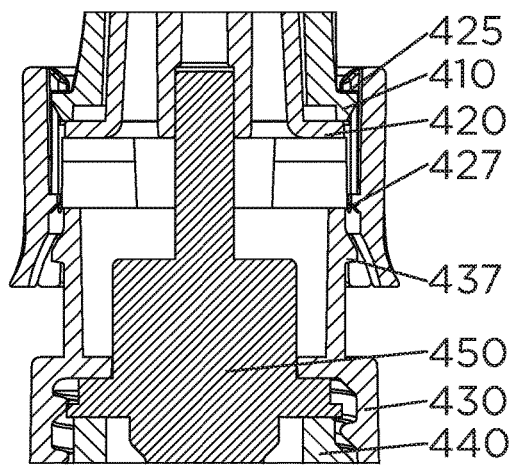
FIG. 29 is a portion of a sectional view of the system taken in the xz-plane to show an unlocked position.
Figure 30:
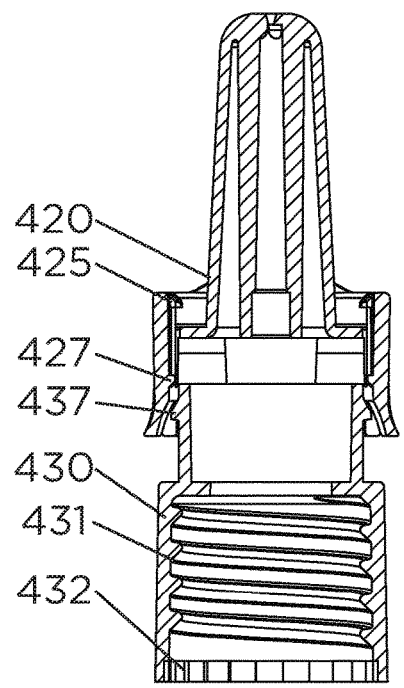
FIG. 30 is sectional view of the dispenser tip and base taken in the xz-plane to show an unlocked position.

FIG. 27 is a portion of a sectional view of the system taken in the xz-plane to show a locked position, FIG. 28 is sectional view of the cap, dispenser tip and base taken in the xz-plane to show a locked position, FIG. 29 is a portion of a sectional view of the system taken in the xz-plane to show an unlocked position, and FIG. 30 is sectional view of the dispenser tip and base taken in the xz-plane to show an unlocked position. FIGS. 27-30 should be generally referred to for the following discussion.

With the cap 410 in place seated in cutout 424 and the dispenser 420 depressed, dispenser actuation is locked out. Specifically, the cap 410 is retained by the top undercuts 425 on the end of levers 422 that act as the release/retention mechanism. The undercuts 425 engage with the topside of the cap 410 to hold it in place. When engaging, the levers 422 will deflect outwards until the undercuts 425 pass the platform of the cap 410, where they will snap back to vertical and engage.

The same lever 422 controls the lockout of the dispensing tip 420. There is a second set of undercuts 427, each on the back side of its corresponding lever within the interior of dispenser 420, that provides the platform for the thread retention of horizontal thread rim 437 on base 430. When engaging, the levers 422 will deflect outwards until the undercuts 427 pass the horizontal thread 437, where they will snap back to vertical and engage.

To release the cap 410/dispensing tip 420, the levers 422 on the dispensing tip 420 must be pressed simultaneously, causing the levers 422 to once again deflect outwards. The dispensing tip 420 will pop up to dispensing mode (under spring pressure of the internal sprayer pump unit 450) and the cap 410 can be drawn up and off of the dispenser tip 420. With the cap 410 having been removed (as shown in FIG. 30), the shoulders 421 can now be depressed to actuate the sprayer pump unit 450 to dispense a single dose. For each subsequent dose, the act of simultaneously depressing the levers 422 must be repeated to release the dispensing tip 420.

Figure 31:
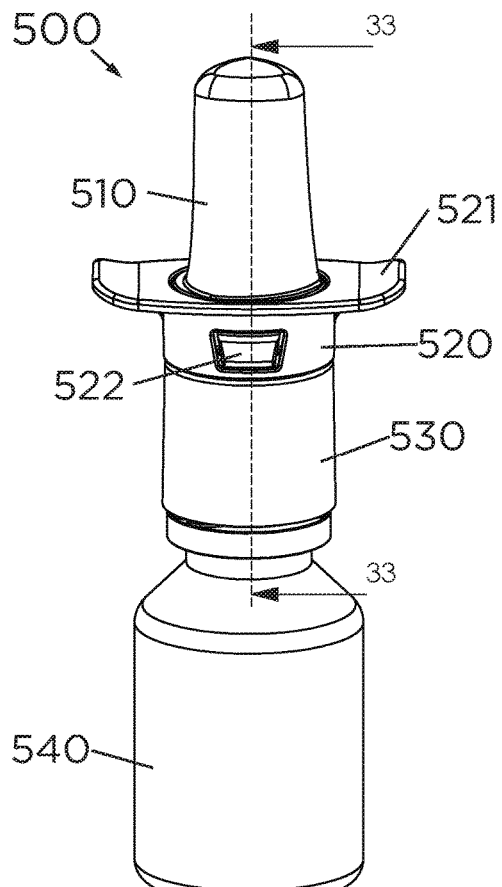
FIG. 31 is a front view of a child-resistant closure system for a pump sprayer according to another example embodiment.

FIGS. 28 and 30 also show the internal threads 431 and serrations 432 on the inside of the base 430. As previously shown in FIGS. 5-8, an anti-back off feature is added to both the bottle 440 and base 430. Upon full seating of the base 430 to the bottle 440, the downward force of application will push the bottom skirt of the bottle (containing serrations 432) over the formed teeth in the bottle 440, providing a secure method of application where tampering to remove the base 430 would be evident and would eliminate accidental removal thereof FIG. 31 is a front view of a child-resistant closure system for a pump sprayer according to another example embodiment. The child-resistant closure (CRC) system 500 is essentially identical to that described above regarding system 300 in FIGS. 16-22. However, unlike system 300, the dispenser tip 520 in system 500 has a double walled construction to increase strength and robustness of the dispenser tip 520, with an outer dispenser cap 520 and an inner wall 520'. As such, the following figures are provided merely to review operation for locked and unlocked conditions of the system.

Figure 32:
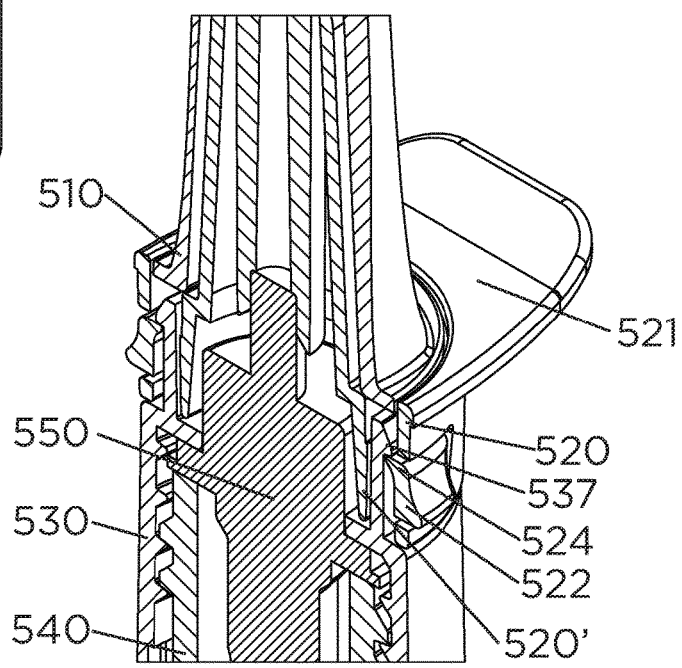
FIG. 32 is a portion of a sectional view of the system taken in the xz-plane to show a locked position.

FIG. 32 is a portion of a sectional view of the system taken in the xz-plane to show a locked position, FIG. 33 is a sectional view 33-33 taken from FIG. 31 to show a locked position, and FIG. 34 is a sectional view 33-33 taken from FIG. 31 to show an unlocked position. Referring to FIGS.

32-34, in the 33-33 view of FIG. 34, the cap 510 is shown removed. This is because in this embodiment the cap 510 is not locked; it can be removed from the dispensing tip 520 by simply pulling upward. With the dispensing tip 520 in place, dispensing actuation is locked out. Specifically, the dispensing tip 520 is retained by the two undercuts 524 on the back face of two buttons 522 180° apart on the base 520. The undercuts 524 engage with the underside of continuous horizontal thread 537 on the base 530, as shown in the locked configuration of FIG. 33. When engaging, the undercuts 524 will initially deflect outwards until they pass the thread 537, where after they will snap back to vertical and engage the underside of thread 537 of base 550, as shown.

To release the dispensing tip 520, the buttons 522 on the dispensing tip 520 must be pressed simultaneously, causing the undercuts 524 to once again deflect outwards. The dispensing tip 520 will move vertically (by force of a spring in the sprayer pump unit 550) to the home dispensing position. This vertical movement is shown in FIG. 34. With the dispensing tip 520 now released, the sprayer pump unit 550 is now free to dispense a single dose. For each dose, the dispensing tip 520 must be released by simultaneously pressing buttons 522.

Figure 35:
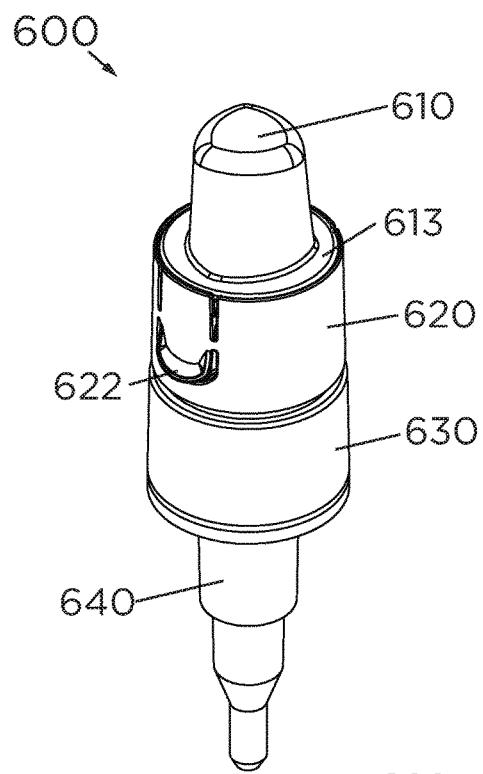
FIG. 35 is a perspective view of a child-resistant closure system for a pump assembly according to another example embodiment.
Figure 37:
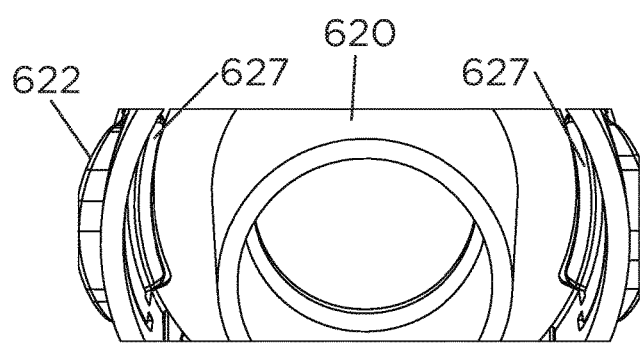
FIG. 37 is a partial bottom perspective view of the dispenser of FIG. 35.
Figure 36:
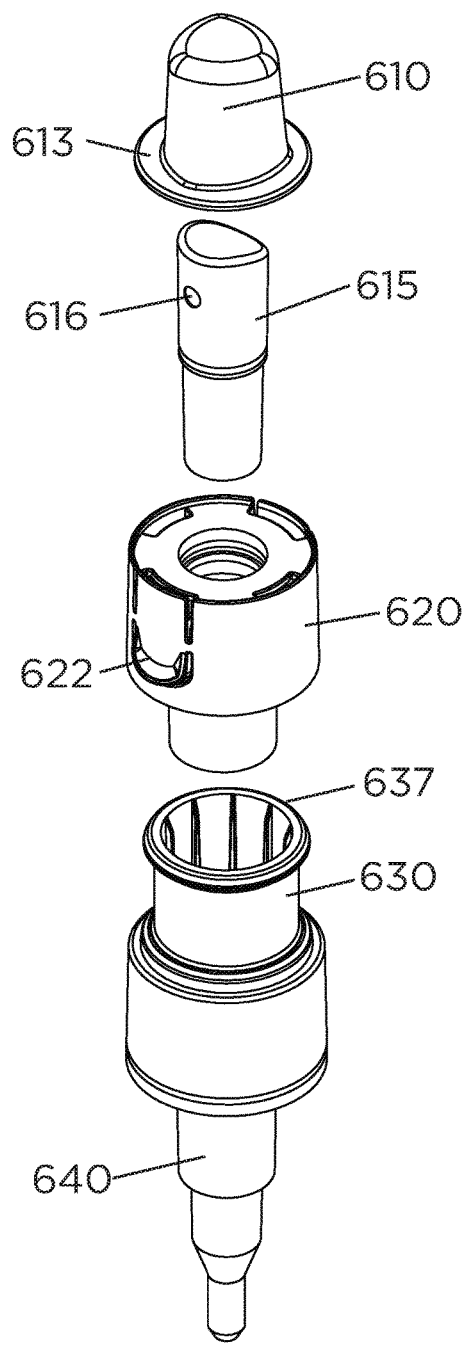
FIG. 36 is an exploded view of the system of FIG. 35.

FIGS. 33 and 34 also show the internal threads 531 and serrations 532 on the inside of the base 530. As previously shown in FIGS. 5-8, an anti-back off feature is added to both the bottle 540 and base 530. Upon full seating of the base 530 to the bottle 540, the downward force of application will push the bottom skirt of the bottle (containing serrations 532) over the formed teeth in the bottle 540, providing a secure method of application where tampering to remove the base 530 would be evident and would eliminate accidental removal thereof FIG. 35 is a perspective view of a child-resistant closure system for a pump assembly according to another example embodiment FIG. 36 is an exploded view of the system of FIG. 35, and FIG. 37 is a partial bottom perspective view of the dispenser of FIG. 35. System 600 differs from the previous embodiments in that CR is provided for a spray pump, with a spray head 615 and nozzle 616. Additionally, the cap 610 serves no part in the child resistance, it can be pulled off at any time.

System 600 includes cap 610, having a flat rim 613 to be seated in dispenser 620, a pump head 615 with nozzle 616, base 630, and tank 640 with or without fluid therein. The dispenser 620 includes a button 622 that actuates similar to the button described in system 400, as it includes a pair of undercuts 627, each on a back side of a corresponding button 622 for engaging the single thread 637 at the top of base 630.

Figure 38:
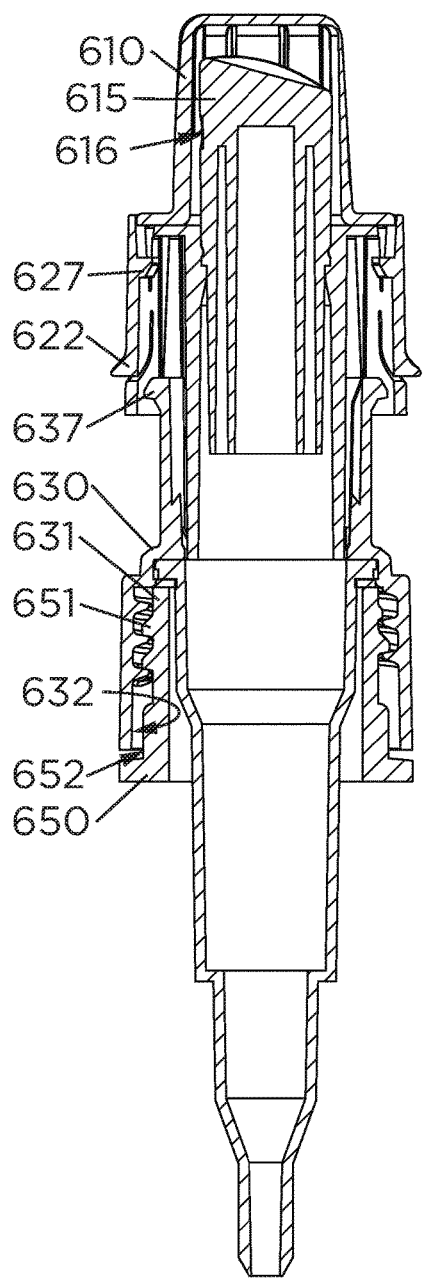
FIG. 38 is a sectional view of the system taken in the xy-plane to show an unlocked position with the cap installed.

FIG. 38 is a sectional view of the system taken in the xy-plane to show an unlocked position with the cap installed. The cap 610 is not locked in this embodiment and is removed by simply pulling upward. FIG. 38 shows the thread 637 disengaged from the undercuts 627 on the back of buttons 622; the dispenser is released and unlocked. However, assuming the dispenser 620 and cap in place, the pump head 615 is locked out. Specifically, the dispenser 620 is retained by the two undercuts 627 on the back face of two buttons 622 on the dispenser 620 that are 60° apart. The undercuts 627 engage with the underside of continuous horizontal thread 637 at the top of the base 630. When engaging, the undercuts 627 will deflect outwards until the undercuts 627 pass the thread 637 where they will snap back to vertical and engage.

To release the dispenser, the buttons 612 must be pressed simultaneously, causing the undercuts 627 to once again deflect outwards and the dispenser 620 will move vertically (by force of the spring in the pump head 615) to the home dispensing position. With the dispenser 620 released, the pump head 615 is now free to dispense one dose.

The example embodiments being thus described, it will be obvious that the same may be varied in many ways. Such variations are not to be regarded as departure from the example embodiments, and all such modifications as would be obvious to one skilled in the art are intended to be included herein.

We claim:

1. A child-resistant closure system for a container, comprising:
   a protective cap;
   a dispensing tip configured to receive the cap thereon, a lower end of the dispensing tip including a pair of finger-depressing shoulders in opposite relation to one another, each shoulder extending horizontally outward from a horizontal circumferential portion of the dispensing tip, a pair of spaced apart slots defined in the horizontal circumferential portion of the dispensing tip, a cylindrical portion provided beneath the shoulders to serve as a bottom end of the dispensing tip, the cylindrical portion including a pair of buttons spaced 180° apart on a vertical facing of the cylindrical portion, the buttons adapted to control whether the dispensing tip is in a locked condition so as to prevent actuation or an unlocked condition so as to permit actuation, via the shoulders, of a sprayer pump unit that is partially contained within the dispensing tip;
   a cylindrical base having its upper end secured to the dispensing tip and its lower end configured to be secured to a dispenser bottle which contains fluid, the dispensing tip and base housing the sprayer pump unit therein which is actuated by depressing the shoulders on the dispensing tip once the dispensing tip is in an unlocked condition, the base top end including a circular ridge formed partly around its circumference on an external surface thereof and a pair of spaced apart upwardly extending legs;
   wherein the dispensing tip is selectively rotatable relative to the base between a locked condition and an unlocked condition;
   wherein, in the locked condition of the dispensing tip, the upwardly extending legs are not aligned with the slots defined in the horizontal circumferential portion of the dispensing tip such that downward movement of the dispensing tip in relation to the base is blocked by the upwardly extending legs to prohibit actuation of the sprayer pump unit and to lock the dispensing tip; and
   wherein, in the unlocked condition of the dispensing tip, the upwardly extending legs are aligned with the slots defined in the horizontal circumferential portion of the dispensing tip such that downward movement of the dispensing tip in relation to the base is not blocked and such that each of the upwardly extending legs protrudes through a corresponding one of the slots defined in the horizontal circumferential portion of the dispensing tip when the dispensing tip moves downward in relation to the base.

2. The child-resistant closure system of claim 1, wherein the dispensing tip further includes a pair of spaced apart protrusions within the cylindrical portion, each of the protrusions being aligned with a corresponding one of the upwardly extending legs when the dispensing tip is in the locked condition such that the protrusions contact the upwardly extending legs when downward movement of the dispensing tip in relation to the base is attempted to block such downward movement of the dispensing tip in relation to the base.

3. The child-resistant closure system of claim 1, wherein, to achieve an unlocked condition of the dispensing tip to permit actuation of the sprayer pump unit via depressing the shoulders, the buttons are pressed simultaneously to permit rotation of the dispensing tip relative to the base from the locked condition to the unlocked condition.

4. The child-resistant closure system of claim 3, wherein each button comprises a first end and second end separated by a vertical hinge, such that depressing the first end inward causes the second end to pivot outward;
   wherein each button comprises a vertical protrusion on an internal side of the second end;
   wherein the vertical protrusion of each button engages with a respective one of the upwardly extending legs when the respective first end is not depressed, thereby preventing rotation of the dispensing tip relative to the base from the locked condition to the unlocked condition; and
   wherein the vertical protrusion of each button disengages from a respective one of the upwardly extending legs when the respective first end is depressed, thereby allowing rotation of the dispensing tip relative to the base from the locked condition to the unlocked condition.

5. The child-resistant closure system of claim 4, wherein each upwardly extending leg comprises an outwardly projecting vertical protrusion; and
   wherein the outwardly projecting vertical protrusion of each upwardly extending leg engages the vertical protrusion of a respective one of the buttons when the respective first end is not depressed.

6. The child-resistant closure system of claim 4, wherein spaced apart gaps are defined in the circular ridge formed partly around the circumference of the top end of the base, each of the gaps being aligned with the vertical protrusion of a respective one of the buttons when the dispensing tip is in the unlocked condition, thereby allowing the dispensing tip to move downward in relation to the base.

* * * * *